United States Patent [19]

Lang et al.

[11] Patent Number: 5,512,276
[45] Date of Patent: Apr. 30, 1996

[54] COMPOSITION FOR FIXING HAIR BASED ON LIGNIN OR LIGNIN DERIVATIVES AS WELL AS DIHYDROXYPROPYL LIGNIN

[75] Inventors: Günther Lang, Reinheim; Thomas Clausen, Alsbach; Hans-Jügen Titze, Gross-Bieberau; Karin Steinbrecht, Darmstadt; Wolfgang Keil, Frankfurt, all of Germany

[73] Assignee: Wella Aktiengesellschaft, Darmstadt, Germany

[21] Appl. No.: 211,797

[22] PCT Filed: Jul. 27, 1993

[86] PCT No.: PCT/EP93/01990

§ 371 Date: Apr. 18, 1994

§ 102(e) Date: Apr. 18, 1994

[87] PCT Pub. No.: WO94/05249

PCT Pub. Date: Mar. 17, 1994

[30] Foreign Application Priority Data

Aug. 29, 1992 [DE] Germany .......................... 42 28 897.5

[51] Int. Cl.$^6$ ..................................................... A61K 7/11
[52] U.S. Cl. ........................... 424/70.11; 424/47; 424/74; 424/401; 514/944; 530/500
[58] Field of Search ................................. 424/70, 71, 401, 424/70.11, 74, 401, 47; 530/500

[56] References Cited

U.S. PATENT DOCUMENTS 4,803,255  7/1989  Pruett et al. ............................ 527/400
4,918,167  4/1990  Glasser et al. ......................... 530/502

FOREIGN PATENT DOCUMENTS 85107583  4/1987  China .
232099  7/1944  Switzerland .

OTHER PUBLICATIONS

European Polymer Journal, vol. 24, No. 9, 1988, pp. 843–847, Dournel, et al.

Journal of Applied Polymer Science, vol. 29, No. 5, pp. 1111–1123, Glasser, et al.

Wood And Agricultural Residues–Research On Use For Feed, Fuels And Chemicals 1983, pp. 149–166, Glasser, et al.

Journal Of Applied Polymer Science, vol. 29, No. 5, pp. 1815–1830, Glasser, et al.

*Primary Examiner*—Jyothsan Venkat
*Attorney, Agent, or Firm*—Michael J. Striker

[57] ABSTRACT

The aqueous, alcoholic or aqueous/alcoholic composition for fixing hair includes from 1.0 to 10 percent by weight of a sulfur-free lignin, which can be hydroxypropyl lignin, hydroxybutyl lignin, dihydroxypropyl lignin and/or mixtures thereof; from 1 to 15% by weight of a film-forming polymer; and a solvent including water, an alcohol having one to four carbon atoms and/or mixtures thereof. It can be in the form of an aerosol hair spray, a non-aerosol hair spray, a non-aerosol foam or a non-aerosol hair lacquer. The composition can also include 2 to 80 percent by weight of a propellant.

12 Claims, No Drawings

COMPOSITION FOR FIXING HAIR BASED ON LIGNIN OR LIGNIN DERIVATIVES AS WELL AS DIHYDROXYPROPYL LIGNIN

This application is a 371 of PCT/EA93/01990 filed Jul. 27, 1993.

BACKGROUND OF THE INVENTION

The invention relates to a composition for fixing hair containing sulfur-free lignin and/or at least one sulfur-free lignin derivative as well as the new sulfur-free lignin derivative dihydroxypropyl lignin.

Compositions for fixing hair conventionally contain solutions of film-forming natural or synthetic polymers. Some examples of the polymers employed are anionic polymers such as acrylic acid or methacrylic acid homopolymers or copolymers, copolymers of acrylic acid and acrylamides and copolymers based on alkyl vinyl ethers and maleic acid monoalkylesters, amphoteric polymers such as copolymers from octylacrylamide, acrylate and butylamino ethyl methacrylate, nonionic polymers such as vinylpyrrolidone homopolymers, vinylpyrrolidone/vinyl acetate copolymers and copolymers of vinylpyrrolidone, vinyl acetate and vinyl propionate.

Polymers suitable for use in compositions for fixing hair must satisfy a great number of requirements. For example, they must be easily soluble in alcohols and alcohol-water mixtures and compatible with commonly used aerosol propellants.

Further, they must form a clear, shiny film on hair and provide hair with a firm but flexible hold without impairing the natural feel of the hair. These polymers must also be stable toward atmospheric humidity so that they retain their holding properties in high humidity and so that the hair does not feel sticky. However, these polymers must be washed out or brushed out of the hair again easily without leaving residue.

To achieve these characteristics, these polymers are often combined with certain additives such as emollients or waterproofing agents. Polymers containing free acid groups are made easier to wash out of the hair by neutralizing the acid groups. However, these steps reduce the hardness of the polymer films.

Synthetic hair-fixing polymers are preferably produced by radical polymerization from monomeric petrochemical products, i.e. from nonrenewable raw materials. In addition, synthetic polymers may contain impurities of monomers, polymerization stoppers and polymerization regulators with objectionable toxicological properties.

Natural polymers do not have the disadvantages of synthetic polymers mentioned above. Shellac, polysaccharides and derivatives of polysaccharides, particularly cellulose derivatives, are natural polymers used for fixing hair. However, hair fixing agents based on shellac are difficult to wash out or brush out and polysaccharide solutions cannot be used in hair sprays because of their high viscosity.

Although a large number of natural and synthetic polymers with various properties are known, it has not been possible thus far to provide a composition for fixing hair which is fully satisfactory in all respects—particularly with respect to holding action, ease of washing or brushing out and resistance to atmospheric humidity.

SUMMARY OF THE INVENTION

Therefore, it is an object of the present invention to provide a composition for fixing hair which does not have the disadvantages of the known compositions, that is, which produces a better hold for the hair, is more stable toward atmospheric humidity and, at the same time, can be washed out of the hair more easily.

Surprisingly, it has now been found that all of the requirements imposed on such compositions are met in an outstanding manner by a composition for fixing hair containing sulfur-free lignin and/or at least one sulfur-free lignin derivative.

The subject matter of the present invention is therefore a composition for fixing hair which is characterized in that it contains sulfur-free lignin and/or at least one sulfur-free lignin derivative.

Sulfur-free lignin is obtained, for example, by the Organocell process (Organocell, Gesellschafi fur Zellstoff- und Umwelttechnik mbH, Munich) by extraction from wood with a methanol-water mixture in pulp processing. The most commonly used method in the paper industry for producing pulp, the sulfite and sulfate processes, provides sulfur-containing lignin.

The sulfur-free raw lignin is preferably purified for use in the composition according to the invention by stirring for 2 to 12 hours at 20° to 40° C. with an organic solvent, preferably with an organic ketone such as acetone or methyl ethyl ketone, or with an alcohol such as methanol, propanol, butanol or the corresponding iso-alcohols, but ethanol is particularly preferred. The insoluble residues in the organic solvent are then removed by filtration or centrifuging and the obtained extraction solution is reduced by distilling the solvent until dry.

In particular, at least one of the compounds hydroxypropyl lignin, hydroxybutyl lignin and dihydroxypropyl lignin is preferably contained as a sulfur-free lignin derivative in the composition, according to the invention, for fixing hair.

Sulfur-free hydroxypropyl lignin and hydroxybutyl lignin are known and may be produced, for example, by the production methods described in Leo C.-F. Wu et al., "Engineering Plastics from Lignin. I., Synthesis of Hydroxypropyl Lignin", J. Appl. Pol. Sci. 29 (1984), pages 1111 to 1123, Wolfgang G. Glasser et al., "Engineering Plastics from Lignin. II., Characterization of Hydroxyalkyl Lignin Derivatives", J. Appl. Sci. 29 (1984), pages 1815 to 1830, and in Wolfgang G. Glasser et al., "Synthesis, Structure and some Properties of Hydroxypropyl Lignins", Wood and Agricultural Residues—Research on use for Feed, Fuels and Chemicals (1983), pages 149 to 166.

The compound dihydroxypropyl lignin which can be contained in the compositions according to the invention is new and is therefore also the subject of the invention.

Dihydroxypropyl lignin is produced by dissolving sulfur-free lignin purified by the methods described above in an organic solvent, preferably in 50-percent aqueous ethanol, reacting with 2,3-epoxy-1-propanol at a temperature of 20° to 100° C., preferably at 40° to 80° C., for 2 to 14 hours, preferably 24 hours, and then reducing the reaction product by distilling the organic solvent until dry, absorbing the remaining reaction product in water, and subsequently filtering the precipitate containing dihydroxypropyl lignin from the water.

The composition according to the invention preferably contains 1 to 10 percent by weight sulfur-free lignin and/or at least one sulfur-free lignin derivative. In a particularly preferred embodiment form, the composition according to the invention contains 1 to 15 percent by weight, preferably 1 to 12 percent by weight, of at least one other natural film-forming polymer and/or a synthetic film-forming polymer in addition to the sulfur-free lignin and/or at least one sulfur-free lignin derivative.

More particularly, the weight ratio of the sulfur-free lignin and/or at least one sulfur-free lignin derivative to the other natural film-forming polymer and/or the synthetic film-forming polymer is preferably 1:20 to 4:1.

Some examples of natural film-forming polymers which can be additionally contained in the composition according to the invention are chitosan, chitosan derivatives such as hydroxypropyl chitosan and hydroxybutyl chitosan, shellac, alginates, gelatins, pectins, and cellulose derivatives such as hydroxypropyl cellulose and hydroxyethyl cellulose.

Some examples of the synthetic film-forming polymers which can be used are polyvinylpyrrolidone, polyvinyl acetate, polyacrylic compounds such as acrylic acid polymers or methacrylic acid polymers, basic polymers of esters of acrylic acid or methacrylic acid with amino alcohols or the salts or quaternization products of these basic polymers, polyacrylonitrile and copolymers or terpolymers of such compounds, e.g. polyvinylpyrrolidone/vinyl acetate.

The film-forming polymers additionally contained in the composition according to the invention, insofar as these polymers contain acid groups, can be neutralized from 50 to 100% with organic amines or alkanolamines, preferably with 2-amino-2-methyl-1-propanol, 2-amino-1-butanol or triisopropylamine.

The composition for fixing hair, according to the invention, is in the form of an aqueous, alcoholic or aqueous-alcoholic preparation, in particular a foam, cream, emulsion, lotion or gel.

In particular, alcohols with 1 to 4 carbon atoms conventionally used for cosmetic purposes, e.g. ethanol and isopropanol, can be used as alcohols. These alcohols can be contained in the composition according to the invention in quantities of 10 to 98 percent by weight, preferably in a quantity of 20 to 90 percent by weight.

The composition for fixing hair, according to the invention, can be put in a pressurized container with a propellant and sprayed as an aerosol or foam. It can also take the form of a non-aerosol hair spray, non-aerosol foam or non-aerosol hair lacquer which can be sprayed by a suitable mechanically operated spraying device.

Mechanical spray devices refer herein to devices which can be used to spray a liquid without the use of a liquified propellant. For example, a suitable mechanical spray device can be a spray pump or a flexible container which is provided with a spray valve and contains the cosmetic composition described above under pressure. This flexible container expands and the composition can be dispensed in a continuous manner from this container due to the contraction of the flexible container when opening the spray valve.

When the composition according to the invention is in the form of an aerosol hair spray, aerosol foam or aerosol hair lacquer it contains, in addition, 2 to 80 percent by weight of a propellant and is introduced into a pressurized container. Some examples of suitable propellants are highly volatile hydrofluorochlorocarbons such as difluorochloromethane or trichloromonofluoromethane, tetrafluorodichloroethane or low alkanes such as n-butane, i-butane and propane, or dimethyl ether and other gaseous propellants, e.g. $N_2$, $N_2O$ and $CO_2$, at the appropriate pressures, as well as mixtures of the aforementioned compounds. Of the propellants mentioned above, dimethyl ether and mixtures of low alkanes with dimethyl ether are preferred. Dimethyl ether is particularly preferred as propellant.

Further, the composition for fixing hair, according to the invention, can contain common cosmetic additives such as anionic, cationic, amphoteric or nonionic wetting agents and emulsifiers, e.g. $C_{12}$- to $C_{18}$-alkyl ether sulfates, alkyltrimethylammonium salts, alkylpyridinium salts, carboxyl derivatives of imidazole, N-alkylsulfobetaine or polyglyceryl ether of saturated or unsaturated fatty alcohols and alkylphenols in quantities of approximately 0.01 to 3 percent by weight, as well as preservatives such as salicylic acid or mandelic acid in quantities of 0.01 to 0.7 percent by weight, anti-dandruff ingredients such as zinc pyridinethion, cosmetic dyes such as fluorescein sodium salt, hair-grooming ingredients such as fatty acid esters, fatty alcohols, fatty acid glycerides, lanolin derivatives or pantothenic acid in quantities of approximately 0.01 to 3 percent by weight, waterproofing agents such as silicone oils, e.g. polydimethylsiloxane, polymethylphenylsiloxane or cyclomethicone, emollients such as phthalic acid ester or alkyl citrates and agents for facilitating combing such as cetyltrimethylammonium chloride, or cationic polymers such as cationic chitosan derivatives or cellulose derivatives in quantities of 0.01 to 0.2 percent by weight, as well as complexing agents, foam stabilizers, buffers, light stabilizers or perfume oils in quantities of approximately 0.01 to 0.8 percent by weight.

The composition for fixing hair according to the invention can simultaneously dye or tint the hair, if desired, by containing cosmetic dyes. Such preparations are known commercially as dyeing and holding compositions or tinting and holding compositions, etc. They contain known direct-dyeing cosmetic dyestuffs commonly used in hair fixing compositions, e.g. aromatic nitro dyes such as 1,4-diamino-2-nitrobenzene, picramic acid, 1-hydroxy-2-amino-4-nitrobenzene and 1,4-bis-(2-hydroxyethyl)amino-2-nitro-5-chlorobenzene, azo dyes such as Acid Brown 4 (C.I. 14,805), anthraquinone dyes such as Disperse Violet 4 (C.I. 61,105) or triphenylmethane dyes such as Basic Violet 1 (C.I. 42,535). Depending on their substituents, the dyes of these classes may have an acidic, nonionic or basic character. The total concentration of these dyes is generally approximately 0.01 to 2.0 percent by weight.

The composition for fixing the hair according to the present invention, while providing an outstanding hold, simultaneously improves the shine and feel of the hair and can be brushed out or washed out easily. Further, hair treated with this composition does not feel sticky at high atmospheric humidity.

Moreover, the composition according to the invention with the additional natural film forming polymers and/or synthetic film-forming polymers contained in a preferred embodiment form exhibit a synergistic effect bringing about increased film hardness and resistance of the polymer films to water vapor.

The following examples explain the subject matter of the invention in more detail.

EXAMPLES

Production Example 1

Purification of sulfur-free raw lignin from spruce (pina abies)

30 kg sulfur-free raw lignin from spruce (pina abies) are stirred with 100 l absolute ethanol for 4 hours at 25° C. The precipitate is then filtered through a filter press and the filtrate is reduced until dry by distilling the ethanol. 15 kg of clear soluble sulfur-free lignin in acetone and ethanol are obtained.

To determine the pendulum hardness of a film of sulfur-free lignin, 20 ml of a 3.8-percent solution of the sulfur-free lignin in ethanol are dried on a glass plate and after preliminary drying at 105° C. for three hours and acclimatization at 20° C. at 35 percent relative humidity, the pendulum hardness was determined according to König (W. König, "Measuring Hardness with the Pendulum Hardness Tester", Farbe und Lack 65 (1959), pages 435 to 433; DIN 53157). A shiny, smooth, dark-brown film is formed. The water vapor absorption was determined at 70% relative humidity compared with 35% relative humidity.

| | |
|---|---|
| Pendulum hardness: | 154 s |
| Water vapor absorption: | 1.7% |

Production Example 2

Dihydroxypropyl lignin 25 g of the sulfur-free lignin purified according to Production Example 1 are dissolved in 200 ml 50-percent aqueous ethanol, mixed with 22.5 g 2.3-epoxy-1-propanol at 80° Celsius over a period of 1 hour, and stirred for another 23 hours at the same temperature. The obtained reaction mixture is reduced until dry by distilling the solvent and the remaining residue is absorbed in 500 ml water. The precipitate which is insoluble in water is removed by filtration, washed repeatedly with water, and then dried in a vacuum at 50° Celsius. 22 g dihydroxypropyl liginin are obtained in the form of a medium-brown powder which is soluble in methanol, 96-percent ethanol and tetrahydrofuran, but insoluble in water.

Pendulum hardness and water vapor absorption were determined under the conditions described in Production Example 1. A shiny, smooth, dark-brown, but uneven film is formed.

| | |
|---|---|
| Pendulum hardness: | 152 ± 14 s |
| Water vapor absorption: | 2.06%. |

Production Example 3

Hydroxypropyl lignin 50 g of the sulfur-free lignin purified according to Production Example 1 are stirred with 400 ml ethylene glycol dimethyl ether, 36.3 g 42-percent caustic soda solution and 260 ml propylene oxide in an autoclave at 1.47 bar for 24 hours at 70° C. The reaction product is then cooled to room temperature, adjusted to a pH of 7 with concentrated hydrochloric acid, and reduced until dry.

The remaining residue is absorbed in 1000 ml anhydrous ethanol and filtered. After distilling the ethanol, 51.1 g hydroxypropyl lignin is obtained in the form of a light-brown powder which is soluble in ethanol, methanol, isopropanol, acetone and tetrahydrofuran, but insoluble in water.

The pendulum hardness and water vapor absorption were determined according to the conditions described in Production Example 1. A shiny, smooth, dark-brown film is formed.

| | |
|---|---|
| Pendulum hardness: | 157 s |
| Water vapor absorption: | 3.8% |

Production Example 4

Hydroxybutyl lignin 50 g of the sulfur-free lignin purified according to Production Example 1 are stirred with 400 ml ethylene glycol dimethyl ether, 36.3 g 42-percent caustic soda solution and 260 ml butylene oxide in an autoclave at 1.47 bar for 24 hours at 70° C. The reaction product is then cooled to room temperature, adjusted to a pH of 7 with concentrated hydrochloric acid, and reduced until dry.

The remaining residue is absorbed in 1000 ml anhydrous ethanol and filtered. After distilling the ethanol, 39.5 g hydroxybutyl lignin is obtained in the form of a medium-brown powder which is soluble in methanol, ethanol and tetrahydrofuran, but insoluble in water.

The pendulum hardness and water vapor absorption were determined according to the conditions described in Production Example 1. A shiny, smooth, dark-brown, slightly uneven film is formed.

| | |
|---|---|
| Pendulum hardness: | 144 ± 8 s |
| Water vapor absorption: | 1.84% |

Analysis of the Lignin Derivatives of Examples 2 to 4

The thermal decomposition products of the lignin derivatives from Examples 2 to 4 were separated by gas chromatography and then identified with mass spectroscopy (compare "Device Parameters for Pyrolysis-GC/MS of Lignin Derivatives of Examples 2 to 4"). The cleavage products were confirmed by GC/MS of the corresponding reference substances.

Device Parameters for Pyrolysis-GC/MS of Lignin Derivatives of Examples 2 to 4

1) Pyrolyzer:

Pyrola-9 (Pyrol AB, Lund, Sweden)

Pyrolysis temperature: 600° C.

2) Gas Chromatograph:

Capillary gas chromatograph HP 5890A with split/splitless injector (Hewlett Packard)

| | |
|---|---|
| Pressure: | 5.0 bar |
| Column pressure: | 1.04 bar (104 kPa) |
| Column flow rate: | 1.4 ml/min |
| Septum flush: | 3.0 ml/min |
| Split ratio: | 1:35 |
| Column temperature: | 40° C./5 min/20° C. per min/ 250° C./25 min |
| Injector temperature: | 250° C. |
| Carrier gas: | helium |

3) Capillary column

| | |
|---|---|
| Type: | WCOT Fused Silica (Chromapack No. 7752) |
| Liquid phase: | CP-Sil-19 CB |
| Film thickness: | 0.20 μm |
| Inner diameter: | 0.32 mm |
| Outer diameter: | 0.45 mm |
| Length: | 50 m |

4) Mass Spectrometer:

Ion trap detector ITD 700 (Finnigan MAT)

Ionization: Electron impact ionization at 70 eV

In pyrolysis, in addition to the decomposition products of the basic structure of the lignin determined by pyrolysis of lignin from Example 1, the samples of lignin derivatives from Examples 2 to 4 showed characteristic cleavage products which did not occur in the thermal decomposition of lignin from Example 1.

The determined thermal cleavage products may be divided into three homologous series (see Table 1) which embody the reaction products of the same thermal reactions of the lignin derivatives from Examples 2 to 4.

TABLE 1

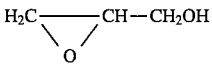

| | Lignin Derivative | Cleavage Product MS (70 eV): m/e (%) |
|---|---|---|
| Series 1 | dihydroxypropyl lignin | 1.2 propanediol 77 (15; $M^+ + 1$) |
| | hydroxypropyl lignin | 2-propanol 59 (3; $M^+ - H$) |
| | hydroxybutyl lignin | 2-butanol 73 (4; $M^+ - H$) |
| Series 2 | dihydroxypropyl lignin | hydroxyacetone 75 (3; $M^+ + 1$) |
| | hydroxypropyl lignin | acetone 58 (9; $M^+$) |
| | hydroxybutyl lignin | 2-butanone 72 (10; $M^+$) |
| Series 3 | dihydroxypropyl lignin | glycerol 93 (25; $M^+ + 1$) |
| | hydroxypropyl lignin | 1,2-propanediol 77 (15; $M^+ + 1$) |
| | hydroxybutyl lignin | 1,2-butanediol 91 (11; $M^+ + 1$) |

Further, glycidol was determined as another cleavage product for dihydroxypropyl lignin.

Examples for Cosmetic Compositions

Example 5

Aerosol hair spray

| 1.0 g | sulfur-free lignin according to Production Example 1 |
| 9.0 g | vinylpyrrolidone/vinyl acetate copolymer |
| 0.1 g | (poly)dimethylsiloxane |
| 0.2 g | paraffin oil |
| 89.7 g | ethanol |
| 100.0 g | |

Example 6

Aerosol hair spray

| 10.0 g | hydroxypropyl lignin according to Production Example 3 |
| 0.1 g | (poly)dimethylsiloxane |
| 0.3 g | paraffin oil |
| 89.6 g | ethanol |
| 100.0 g | |

Example 7

Aerosol hair spray

| 5.0 g | hydroxybutyl lignin according to Production Example 4 |
| 5.0 g | vinylpyrrolidone/vinyl acetate copolymer |
| 0.1 g | (poly)dimethylsiloxane |
| 0.2 g | paraffin oil |
| 89.7 g | ethanol |
| 100.0 g | |

Example 8

Aerosol hair spray

| 2.0 g | sulfur-free lignin according to Production Example 1 |
| 2.0 g | hydroxypropyl cellulose |
| 0.2 g | perfume oil |
| 45.8 g | ethanol |

-continued

| | |
|---|---|
| 50.0 g | dimethyl ether |
| 100.0 g | |

The compositions according to Examples 5, 6, 7 and 8 can be placed in suitable spray containers along with dimethyl ether, for example, as a propellant in a mixture ratio of 45:55.

In all three formulas, a good hold of the hairstyle and a natural feel and appearance are obtained after application.

Example 9

Non-aerosol hair spray

| | |
|---|---|
| 3.8 g | sulfur-free lignin according to Production Example 1 |
| 0.1 g | perfume oil |
| 0.1 g | (poly)dimethylsiloxane with a viscosity of 20 mm$^2 \cdot$ s$^{-1}$ at 25° C. |
| 96.0 g | ethanol |
| 100.0 g | |

Example 10

Non-aerosol hair spray

| | |
|---|---|
| 3.8 g | hydroxypropyl lignin according to Production Example 1 |
| 0.1 g | perfume oil |
| 0.1 g | (poly)dimethylsiloxane with a viscosity of 20 mm$^2 \cdot$ s$^{-1}$ at 25° C. |
| 96.0 g | ethanol |
| 100.0 g | |

Example 11

Non-aerosol hair spray

| | |
|---|---|
| 3.8 g | hydroxybutyl lignin according to Production Example 4 |
| 0.1 g | perfume oil |
| 0.1 g | (poly)dimethylsiloxane with a viscosity of 20 mm$^2 \cdot$ s$^{-1}$ at 25° C. |
| 96.0 g | ethanol |
| 100.0 g | |

Example 12

Non-aerosol hair spray

| | |
|---|---|
| 3.8 g | sulfur-free lignin according to Production Example 1 |
| 0.1 g | perfume oil |
| 0.1 g | (poly)dimethylsiloxane with a viscosity of 20 mm$^2 \cdot$ s$^{-1}$ at 25° C. |
| 80.0 g | ethanol |
| 16.0 g | water |
| 100.0 g | |

Example 13

Non-aerosol hair spray

| | |
|---|---|
| 3.8 g | sulfur-free lignin according to Production Example 1 |
| 0.1 g | perfume oil |
| 0.1 g | (poly)dimethylsiloxane with a viscosity of 20 mm$^2 \cdot$ s$^{-1}$ at 25° C. |
| 90.0 g | ethanol |
| 5.8 g | water |
| 0.2 g | 2-amino-1-methylpropanol |
| 100.0 g | |

Example 14

Non-aerosol hair spray

| | |
|---|---|
| 3.0 g | sulfur-free lignin according to Production Example 1 |
| 2.0 g | hydroxybutyl chitosan |
| 0.2 g | perfume oil |
| 0.1 g | (poly)dimethylsiloxane with a viscosity of 20 mm$^2 \cdot$ s$^{-1}$ at 25° C. |
| 94.7 g | ethanol |
| 100.0 g | |

The compositions according to Examples 9 to 14 are placed in containers from which the composition for fixing hair is applied to the hair by a spray pump.

The use of non-aerosol hair spray according to Examples 9 to 14 provides a good hold of the hairstyle with a natural feel and appearance.

Example 15

Setting composition

| | |
|---|---|
| 1.00 g | sulfur-free lignin according to Production Example 1 |
| 0.40 g | perfume oil |
| 0.05 g | cetyltrimethylammonium chloride |
| 45.00 g | ethanol |
| 53.55 g | water |
| 100.00 g | |

Example 16

Setting composition

| | |
|---|---|
| 1.00 g | hydroxypropyl lignin according to Production Example 3 |
| 0.40 g | perfume oil |
| 0.05 g | cetyltrimethylammonium chloride |
| 45.00 g | ethanol |
| 53.55 g | water |
| 100.00 g | |

Example 17

Setting composition

| | |
|---|---|
| 1.00 g | hydroxybutyl lignin according to Production Example 4 |
| 0.40 g | perfume oil |
| 0.05 g | cetyltrimethylammonium chloride |
| 45.00 g | ethanol |

Example 18

Setting composition

| | |
|---|---|
| 1.00 g | dihydroxypropyl lignin according to Production Example 2 |
| 0.40 g | perfume oil |
| 0.05 g | cetyltrimethylammonium chloride |
| 45.00 g | ethanol |
| 53.55 g | water |
| 100.00 g | |

The setting compositions described above are applied in the usual manner for such compositions in that approximately 20 ml of the composition are distributed in the hair which has already been washed and towel-dried. The hair is then styled and dried. The setting composition according to the invention provides the hair with outstanding hold and thus prolongs the hold of the hairstyle.

Example 19

Styling gel

| | |
|---|---|
| 1.000 g | hydroxypropyl lignin according to Production Example 3 |
| 0.875 g | hydroxypropyl cellulose |
| 0.125 g | cationic cellulose derivative (e.g., Polymer JR ®-400, Union Carbide Co.) |
| 0.300 g | perfume oil |
| 40.000 g | ethanol |
| 57.700 g | water |
| 100.000 g | |

The hydroxypropyl lignin contained in Example 19 can be replaced by the same amount of sulfur-free lignin or hydroxybutyl lignin.

Example 20

Tinting and holding composition

| | |
|---|---|
| 1.00 g | hydroxypropyl lignin according to Production Example 3 |
| 0.15 g | 1,4-di(2'-hydroxyethylamino)-2-nitro-5-clorobenzene |
| 40.00 g | ethanol |
| 58.85 g | water |
| 100.000 g | |

The tinting and holding composition described above is applied in the usual manner for such compositions in that approximately 20 ml of the composition are distributed in the hair which has already been washed and towel-dried. The tinting and holding composition according to the invention dyes hair a red-violet color and gives the hair excellent hold. Comparison Tests 21 to 23

Comparison Examples 23, 24, 26, 27, 29, 30 and 31, according to the invention, in the following Table 1 which contain a combination of sulfur-free lignin and a synthetic film-forming polymer were compared with respect to pendulum hardness and water vapor absorption of the obtained polymer film with Comparison Example 21, according to the invention, which contains only sulfur-free lignin and with the corresponding Comparison Examples 22, 25 or 28 which are not of the invention and which contain only one synthetic film-forming polymer.

The pendulum hardness and water vapor absorption were determined according to the conditions described in Production Example 1. For this purpose, 20 ml of a composition according to Comparison Examples 21 to 31 were used.

TABLE 1

| | 21 | 22 | 23 | 24 | 25 | 26 | 27 | 28 | 29 | 30 | 31 |
|---|---|---|---|---|---|---|---|---|---|---|---|
| sulfur-free lignin according to Production Example 1 | 3.8 g | — | 0.6 g | 1.9 g | — | 0.8 g | 1.9 g | — | 0.4 g | 1.2 g | 1.9 g |
| vinylpyrrolidone/vinyl acetate/vinylpropionate copolymer | — | 3.8 g | 3.2 g | 1.9 g | — | — | — | — | — | — | — |
| vinyl acetate/crotonic acid/vinyl neodecanoate terpolymer | — | — | — | — | 3.8 g | 3.0 g | 1.9 g | — | — | — | — |
| maleic acid butyl ester/methyl vinyl ether copolymer | — | — | — | — | — | — | — | 3.8 g | 3.4 g | 2.6 g | 1.9 g |
| ethanol | 96.2 g | 96.2 g | 96.2 g | 96.2 g | 96.2 g | 96.2 g | 96.2 g | 96.2 g | 96.2 g | 96.2 g | 96.2 g |
| | 100.0 g | 100.0 g | 100.0 g | 100.0 g | 100.0 g | 100.0 g | 100.0 g | 100.0 g | 100.0 g | 100.0 g | 100.0 g |
| pendulum hardness s | 154 | 161 | 179 | 204 | 183 | 193 | 196 | 177 | 179 | 184 | 186 |
| water vapor absorption % | 1.7 | 5.9 | 3.5 | 2.5 | 1.57 | 1.41 | 1.51 | 2.6 | 2.6 | 2.6 | 2.2 |

Comparison Examples 23 and 24, 26 and 27 or 30 and 31 show the synergistic effect of the compositions having a combination of sulfur-free lignin with synthetic film-forming polymers commonly used for such compositions compared with Comparison Example 21 containing only sulfur-free lignin and compared with Comparison Examples 22, 25 and 28 which are not of the invention and contain only a film-forming synthetic polymer which is commonly used for such compositions and manifests itself in an increase in the polymer film hardness and an occasionally disproportionate reduction in water vapor absorption.

Comparison Examples 32 to 43

Comparison Examples 34, 35, 37, 38, 39, 41, 42 and 43, according to the invention, in the following Table 2 which contain a combination of hydroxypropyl lignin and a synthetic film-forming polymer were compared with respect to pendulum hardness and water vapor absorption of the obtained polymer film with Comparison Example 32, according to the invention, which contains only hydroxypropyl lignin and with the corresponding Comparison Examples 33, 36 and 40 which are not of the invention and which contain only a synthetic film-forming polymer.

The pendulum hardness and water vapor absorption of the polymer films were determined in the same manner as in Comparison Examples 21 to 31.

TABLE 2

|  | 32 | 33 | 34 | 35 | 36 | 37 | 38 | 39 | 40 | 41 | 42 | 43 |
|---|---|---|---|---|---|---|---|---|---|---|---|---|
| hydroxypropyl lignin according to Production Example 3 | 3.8 g | — | 1.2 g | 1.9 g | — | 0.4 g | 1.2 g | 1.9 g | — | 0.4 g | 1.2 g | 1.9 g |
| vinylpyrrolidone/vinyl acetate/copolymer | — | 3.8 g | 2.6 g | 1.9 g | — | — | — | — | — | — | — | — |
| vinylpyrrolidone/vinyl acetate/vinyl propionate copolymer | — | — | — | — | 3.8 g | 3.4 g | 2.6 g | 1.9 g | — | — | — | — |
| vinyl acetate/crotonic acid copolymer | — | — | — | — | — | — | — | — | 3.8 g | 3.4 g | 2.6 g | 1.9 g |
| ethanol | 96.2 g | 96.2 g | 96.2 g | 96.2 g | 96.2 g | 96.2 g | 96.2 g | 96.2 g | 96.2 g | 96.2 g | 96.2 g | 96.2 g |
|  | 100.0 g | 100.0 g | 100.0 g | 100.0 g | 100.0 g | 100.0 g | 100.0 g | 100.0 g | 100.0 g | 100.0 g | 100.0 g | 100.0 g |
| pendulum hardness s | 157 | 151 | 166 | 175 | 139 | 160 | 174 | 181 | 116 | 127 | 144 | 171 |
| water vapor absorption % | 3.8 | 4.6 | 3.85 | 3.5 | 5.9 | 5.3 | 4.5 | 3.9 | 2.6 | 2.8 | 2.8 | 3.1 g |

Comparison Examples 34 and 35, 37, 38 and 39 or 41, 42 and 43 show the synergistic effect of the compositions having a combination of hydroxypropyl lignin and synthetic film-forming polymers commonly used for such compositions compared with Comparison Example 32 containing only hydroxypropyl lignin and compared with Comparison Examples 33, 36 and 40 which are not of the invention and contain only a film-forming synthetic polymer which is commonly used for such compositions and manifests itself in an increase in the polymer film hardness and an occasionally disproportionate reduction in water vapor absorption.

All percentages shown in the present application represent percent by weight.

While the invention has been illustrated and described as embodied in a composition for fixing hair base on lignin or lignin derivatives and dihydroxypropyl lignin, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. Composition for fixing hair comprising
   from 1 to 10 percent by weight of a lignin member selected from the group consisting of sulfur-free lignin, hydroxypropyl lignin, hydroxybutyl lignin and dihydroxypropyl lignin and mixtures thereof;
   from 1 to 15% by weight of a film-forming polymer; and
   a solvent selected from the group consisting of water, alcohols having one to four carbon atoms and mixtures thereof.

2. Composition as defined in claim 1, wherein said lignin member and said film-forming polymer are present in a weight ratio of from 1:20 to 4:1.

3. Composition as defined in claim 1, wherein said lignin member is said dihydroxylpropyl lignin.

4. Composition as defined in claim 1, wherein said film-forming polymer is present in an amount of from 1 to 15% by weight and is selected from the group consisting of chitosan; hydroxypropyl chitosan; hydroxybutyl chitosan; shellac; alginates; gelatins; pectins; hydroxypropyl cellulose; hydroxyethyl cellulose; polyvinylpyrrolidone; polyvinyl acetate; polyacrylic compounds; and polyvinylpyrrolidone/vinyl acetate copolymer.

5. Composition as defined in claim 1, in the form of a foam or an aerosol.

6. Composition as defined in claim 1, further comprising 2 to 80 percent by weight of a propellant.

7. Composition as defined in claim 1, in the form of a non-aerosol hair spray or a non-aerosol foam.

8. Composition as defined in claim 1, in the form of a non-aerosol hair lacquer.

9. Composition as defined in claim 1, further comprising from 0.01 to 2 percent of a cosmetic dye.

10. Composition as defined in claim 9, in the form of a dyeing and holding composition.

11. Composition as defined in claim 1, further comprising a cosmetic additive selected from the group consisting of anionic wetting agents, cationic wetting agents, amphoteric wetting agents, anionic emulsifiers, cationic emulsifiers, amphoteric emulsifiers, preservatives, anti-dandruff ingredients, cosmetic dyes, hair-grooming ingredients, waterproofing agents, emollients, complexing agents, foam stabilizers, buffers, light stabilizers and perfume oils.

12. Dihydroxypropyl lignin.

* * * * *